United States Patent
Oh et al.

(10) Patent No.: US 10,912,907 B2
(45) Date of Patent: Feb. 9, 2021

(54) DOUBLE LUMEN TUBE CAPABLE OF FIXING TRACHEA CARINA

(71) Applicant: INSUNG MEDICAL CO., LTD., Wonju-si (KR)

(72) Inventors: Young-jun Oh, Seoul (KR); Hyo-jin Byon, Goyang-si (KR)

(73) Assignee: INSUNG MEDICAL CO., LTD., Wonju-si (KR)

( * ) Notice: Subject to any disclaimer, the term of this patent is extended or adjusted under 35 U.S.C. 154(b) by 224 days.

(21) Appl. No.: 16/081,241

(22) PCT Filed: Mar. 17, 2017

(86) PCT No.: PCT/KR2017/002879
§ 371 (c)(1),
(2) Date: Aug. 30, 2018

(87) PCT Pub. No.: WO2017/160110
PCT Pub. Date: Sep. 21, 2017

(65) Prior Publication Data
US 2019/0070377 A1      Mar. 7, 2019

(30) Foreign Application Priority Data

Mar. 18, 2016  (KR) .................. 10-2016-0032718

(51) Int. Cl.
*A61M 16/04*       (2006.01)
(52) U.S. Cl.
CPC .... *A61M 16/0486* (2014.02); *A61M 16/0404* (2014.02); *A61M 16/0434* (2013.01); *A61M 16/0454* (2014.02)

(58) Field of Classification Search
CPC .......... A61M 16/0486; A61M 16/0404; A61M 16/0454; A61M 16/0443; A61M 16/0445;
(Continued)

(56) References Cited

U.S. PATENT DOCUMENTS 4,819,664 A * 4/1989 Nazari .................. A61M 16/04
                                                  128/207.15
4,840,172 A * 6/1989 Augustine ......... A61M 16/0488
                                                  128/207.14
(Continued)

FOREIGN PATENT DOCUMENTS

JP    2009-125184 A    6/2009
JP    2011-010685 A    1/2011
(Continued)

*Primary Examiner* — Jan Christopher L Merene
*Assistant Examiner* — Brian T Khong
(74) *Attorney, Agent, or Firm* — Patent Office of Dr. Chung Park

(57) ABSTRACT

A double lumen endotracheal tube capable of being fixed to the trachea carina. The double lumen endotracheal tube includes: a first tube extended in one direction; a second tube extended while being adjacent to the first tube and having an extended portion bent toward one side thereof and extended longer than the first tube; a first balloon extended while passing through the first tube so as to expand or contract a first cuff connected to the end thereof; a second balloon extended while passing through the second tube so as to expand or contract a second cuff connected to the end thereof; and a third balloon extended while passing through between the first tube and the second tube so as to expand or contract a third cuff connected to the end thereof.

3 Claims, 5 Drawing Sheets

(58) Field of Classification Search
CPC ............ A61M 16/045; A61M 16/0456; A61M 16/0459; A61M 16/04; A61M 16/0434; A61M 16/0475; A61M 16/0463
See application file for complete search history.

(56) References Cited

U.S. PATENT DOCUMENTS

| | | | | | |
|---|---|---|---|---|---|
| 5,315,992 | A * | 5/1994 | Dalton | .................. | A61M 16/04 128/207.15 |
| 6,609,521 | B1 * | 8/2003 | Belani | .................. | A61M 16/04 128/207.14 |
| 8,757,159 | B2 * | 6/2014 | Nierich | ............. | A61M 16/0486 128/207.14 |
| 2002/0185135 | A1 * | 12/2002 | Amar | .................... | A61M 16/04 128/207.15 |
| 2004/0011364 | A1 * | 1/2004 | Dhuper | ............. | A61M 16/0484 128/207.14 |
| 2007/0017519 | A1 * | 1/2007 | Kuo | .................. | A61M 16/0486 128/204.26 |
| 2012/0000471 | A1 * | 1/2012 | Harrington | ........ | A61M 16/0486 128/207.15 |
| 2012/0172664 | A1 * | 7/2012 | Hayman | ............ | A61B 1/00045 600/109 |
| 2012/0298111 | A1 * | 11/2012 | Wood | ................ | A61M 16/0443 128/207.14 |
| 2013/0092171 | A1 * | 4/2013 | Sederstrom | ........... | A61M 16/04 128/207.15 |
| 2013/0096379 | A1 * | 4/2013 | Goldberg | .............. | A61B 1/2676 600/109 |
| 2013/0158351 | A1 * | 6/2013 | Daher | ............... | A61M 16/0434 600/109 |
| 2016/0213870 | A1 * | 7/2016 | Kumar | .................. | A61M 16/14 |

FOREIGN PATENT DOCUMENTS

| | | |
|---|---|---|
| KR | 10-2007-0108141 A | 11/2007 |
| KR | 10-2008-0033346 A | 4/2008 |
| KR | 10-2011-0027667 A | 3/2011 |

* cited by examiner

DOUBLE LUMEN TUBE CAPABLE OF FIXING TRACHEA CARINA

CROSS-REFERENCE TO PRIOR APPLICATIONS

This application is a national Stage Patent Application of PCT International Patent Application No. PCT/KR2017/002879, filed on Mar. 17, 2017 under 35 U.S.C. § 371, which claims priority of Korean Patent Application No. 10-2016-0032718, filed on Mar. 18, 2016, which are all hereby incorporated by reference in their entirety.

BACKGROUND OF THE INVENTION

Field of the Invention

The present invention relates to a double lumen endotracheal tube, and more particularly, to a double lumen endotracheal tube capable of being fixed to the trachea carina that is used for a lung resection operation and is improved in existing double lumen endotracheal tubes used for ventilation during the lung resection operation to allow a surgeon to accurately expect an inserted depth of the double lumen endotracheal tube into the trachea carina, thereby more effectively performing the ventilation during the lung resection operation.

Background of the Related Art

So as to perform a lung operation, generally, breathing through the lung to be operated stops, and breathing only through the lung to be not operated is conducted. Like this, so as to stop the breathing through the lung to be operated, an endotracheal tube specially designed for the breathing of the corresponding lung is needed.

So as to perform endotracheal intubation to stop the lung breathing, a double lumen endotracheal tube is generally used in conventional practices.

As shown in FIG. 1, the conventional double lumen endotracheal tube 100 is inserted into the main bronchus of the desired side of the lungs, and the lung into which the double lumen endotracheal tube 100 is inserted stops breathing, so that the lung operation can be performed gently. Of course, the double lumen endotracheal tube 100 can perform the lung operation for the corresponding lung, while even stopping breathing through the lung into which the tip thereof is not inserted, but it is not shown in the figure.

The conventional double lumen endotracheal tube 100 has to be mounted to an accurate depth into the main bronchus of the desired lung through intubation, but since the anatomical lungs have the main bronchi and the bronchioles divided from the main bronchi, it is difficult for a surgeon who is not an expert to recognize whether the tip of the endotracheal tube 100 is mounted into the main bronchus to an accurate depth.

Like this, it is not easy to induce intubating to one side from the trachea carina, and as a result, the trachea or bronchus may be damaged.

After the intubation, so as to check whether the double lumen endotracheal tube 100 is mounted to the accurate depth besides, the location of the double lumen endotracheal tube 100 should be additionally checked by means of an endoscope, which is undesirably inconvenient to use.

The prior art related to the present invention is disclosed in U.S. Pat. No. 8,425,455.

SUMMARY OF THE INVENTION

Accordingly, the present invention has been made in view of the above-mentioned problems occurring in the prior art, and it is an object of the present invention to provide to a double lumen endotracheal tube that is capable of being insertedly mounted into the main bronchus to an accurate depth to perform one side lung breathing, while minimizing the damage of the trachea or bronchus.

To accomplish the above-mentioned object, according to the present invention, there is provided a double lumen endotracheal tube including: a first tube extended in one direction; a second tube extended while being adjacent to the first tube and having an extended portion bent toward one side thereof and extended longer than the first tube; a first balloon extended while passing through the first tube so as to expand or contract a first cuff connected to the end thereof; a second balloon extended while passing through the second tube so as to expand or contract second cuff connected to the end thereof; and a third balloon extended while passing through between the first tube and the second tube so as to expand or contract a third cuff connected to the end thereof.

According to the present invention, desirably, the first cuff is adapted to surround the outer peripheral portions of the first tube and the second tube and is expanded in the state of being inserted into the trachea to close the trachea.

According to the present invention, desirably, the second cuff adapted to surround the outer peripheral portion of the extended portion of the second tube and is expanded in the state of being inserted into the main bronchus of one side lung to close the main bronchus.

According to the present invention, desirably, the third cuff is located at a given point between a first end of the first tube and a start point of the second cuff to guide an inserted depth of the extended portion.

According to the present invention, desirably, the third cuff is expanded toward the opposite side lung to one side lung into which the extended portion is inserted.

According to the present invention, desirably, until the third cuff reaches the tracheal carina to allow the extended portion to be inserted into one side lung, the third cuff is kept in the expanded state.

According to the present invention, desirably, the third balloon penetrates a partition wall between the first tube and the second tube in such a manner as to be connected to the third cuff.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Figure 1:
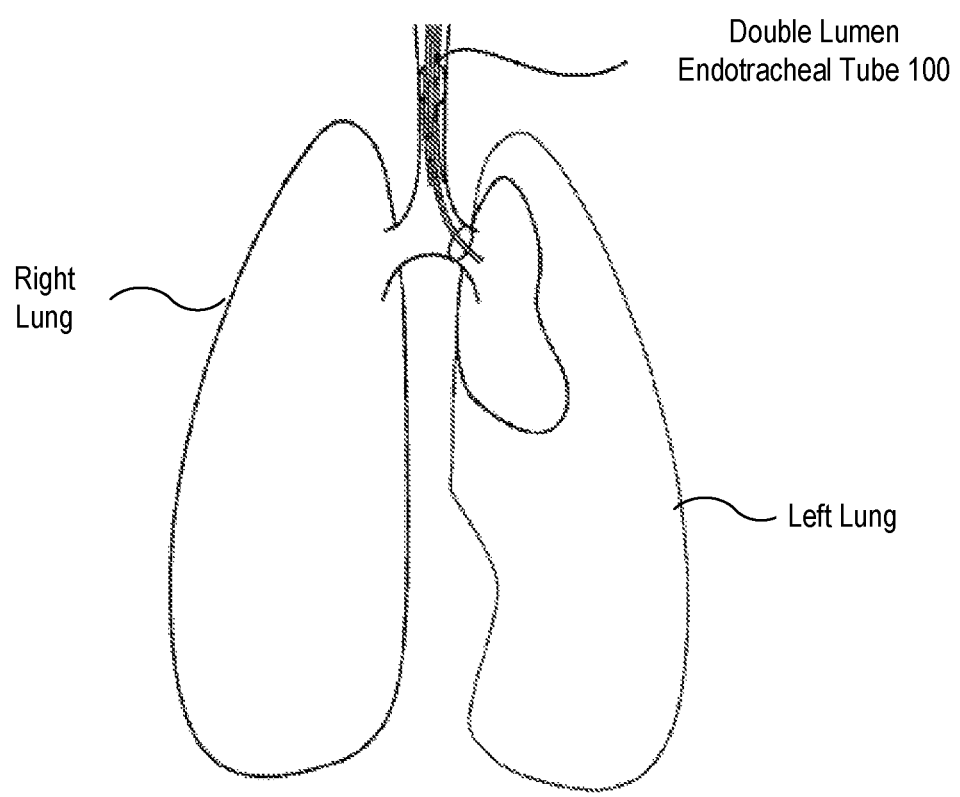
FIG. 1 is an exemplary view showing a state where a conventional double lumen endotracheal tube is inserted into the lung.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention. In the description, it should be noted that the parts corresponding to those of the drawings are indicated by corresponding reference numerals. Terms, such as the first, the second, and so on may be used to describe various elements, but the elements should not be restricted by the terms.

The terms are used to only distinguish one element from the other element. The terminology used herein is for the purpose of describing particular embodiments only and is not intended to be limiting. The term 'a' or 'an', as used herein, are defining as one or more than one. The term 'including' and/or 'having', as used herein are intended to refer to the above features, numbers, steps, operations, elements, parts or combinations, and it is to be understood that the terms are not intended to preclude the presence of one or more features, numbers, steps, operations, elements, parts or combinations and added possibilities.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification.

Hereinafter, an explanation on a double lumen endotracheal tube according to the present invention will be in detail given with reference to the attached drawing.

Figure 2:
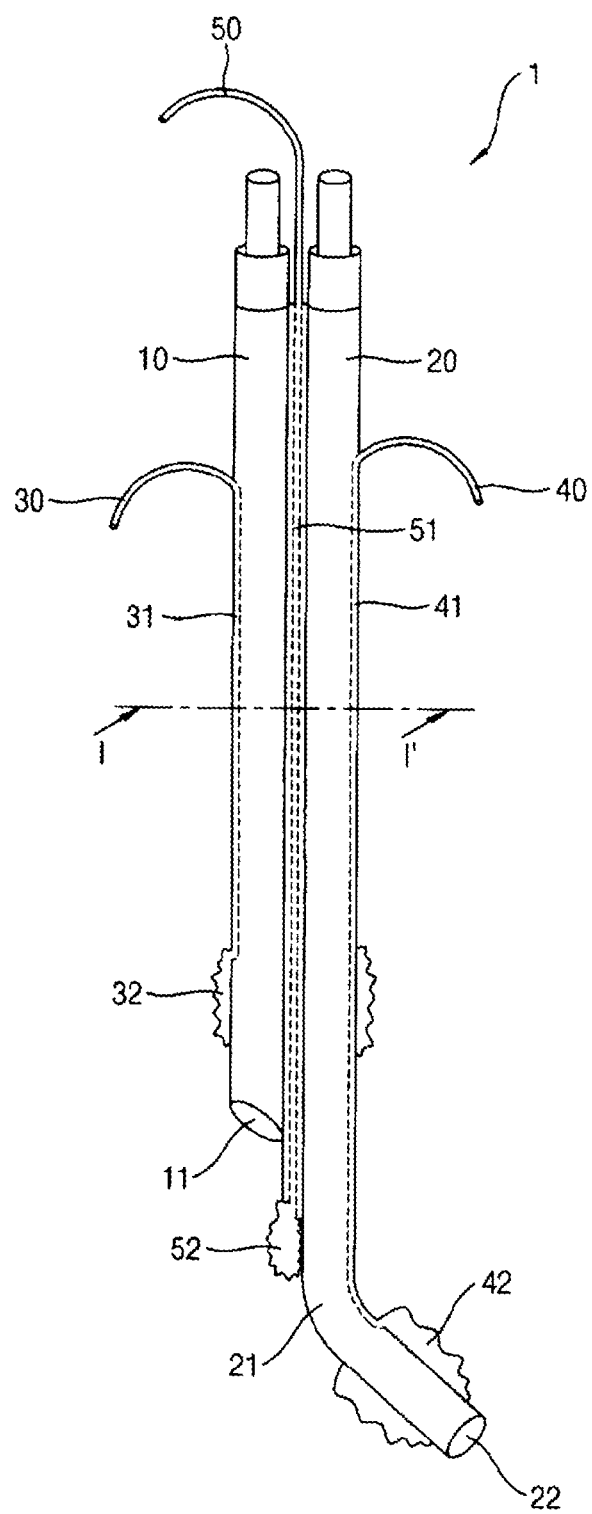
FIG. 2 is a front view showing a double lumen endotracheal tube according to the present invention.
Figure 3:
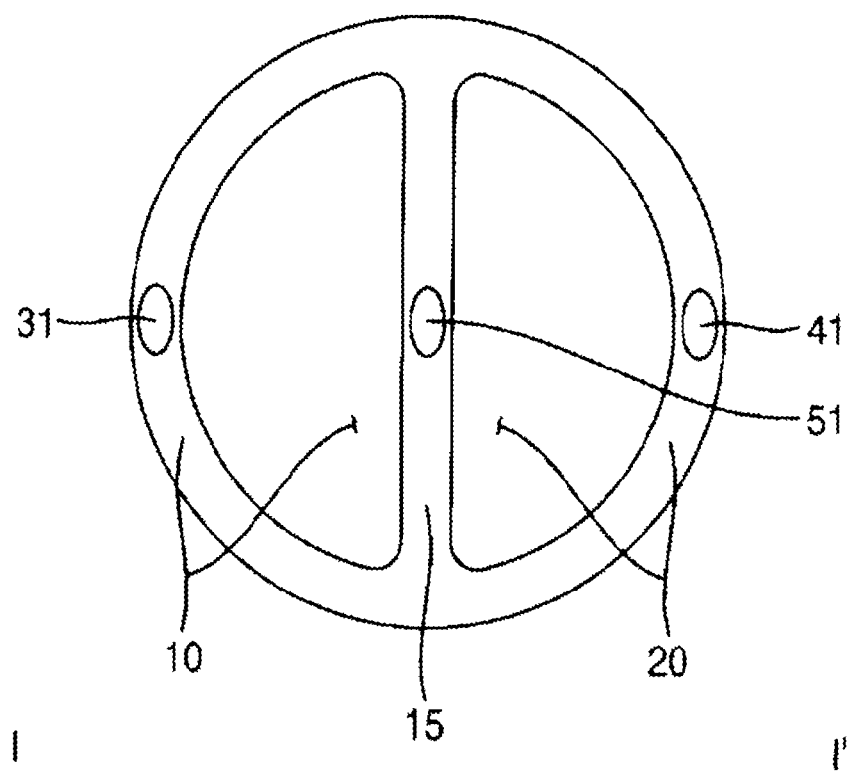
FIG. 3 is a sectional view taken along the line I-I' of FIG. 2.

FIG. 2 is a front view showing a double lumen endotracheal tube according to the present invention. FIG. 3 is a sectional view taken along the line I-I' of FIG. 2.

As shown in FIGS. 2 and 3, a double lumen endotracheal tube 1 according to the present invention includes a first tube 10, a second tube 20, a first balloon 30, a second balloon 40, and a third balloon 50.

The first tube 10 is extended in one direction, and the second tube 20 is extended in the same direction as the first tube 10.

The first use 10 and the second tube 20 are made of a flexible material and bendable along the extended directions thereof. In this case, the first tube 10 and the second tube 20 are fixed to each other by means of a partition wall 15 so that they are bent or extended in the same direction as each other.

The first tube 10 has a first end 11 open thereon. Through the first tube 10, air introduced into one side lung, and contrarily, air is discharged from one side lung to the outside.

The second tube 20 has an extended portion 21 so that it is no longer than the first tube 10. As shown, the extended portion 21 is bentedly extended to one side.

In this case, the extended portion 21 is bent toward the opposite direction to a direction toward the first tube 10, and if the extended portion 21 is inserted into one side lung, accordingly, it is insertedly fitted to any one of two main bronchi.

Further, the second tube 20 has a second end 22 open on the end of the extended portion 21. Through the second tube 20, air is introduced into the lung into which the extended portion 21 is inserted, and contrarily, air is, discharged from the lung to the outside.

The first balloon 30 is extended along the first tube 10 while passing through the first tube 10 in such a manner as to allow the first cuff 32 to be connected to the end thereof.

In more detail, as shown in FIG. 3, the first balloon 30 has a first internal tube 31 disposed to penetrate an outer peripheral wall of the first tube 10, and the first cuff 32 connected to the end of the first internal tube 31.

The first cuff 32 is connected to the end of the first internal tube 31 in such a manner as to be located above the first end 11 the first tube 10 to surround the outer peripheral portions of the first tube 10 and the second tube 20.

If air is injected through the first balloon 30, as a result, the first cuff 32 is expanded uniformly to increase radius of the double lumen endotracheal tube 1 along the first tube 10 and the second tube 20.

On the other hand, the second balloon 40 has a second internal tube 41 disposed to penetrate an outer periphery wall of the second tube 20, and the second cuff 42 is connected to the end of the second internal tube 41.

In this case, the second internal tube 41 is connected to the extended portion 21 of the second tube 20, and accordingly, the second cuff 42 is located above the second end 22 of the second tube 20.

Further, the second cuff 42 surrounds the outer peripheral portion of the extended portion 21.

If air is injected through the second balloon 40, as a result, the second cuff 42 is expanded uniformly to increase the radius of the extended portion 21 along the extended portion 21.

The third balloon 50 has a third internal tube 51 disposed to penetrate the partition wall 15 between the first tube 10 and the second tube 20, and the third cuff 52 is connected to the end of the third internal tube 51.

In this case, the third internal tube 51 is extended to a center between the first end 11 of the first tube 10 and a start point of the second cuff 42, and for example, accordingly, the third cuff is located at a point of the center between first end 11 of the first tube 10 and the start point of the second cuff 42.

If air is injected through the third balloon 50, as a result, the third cuff 52 is expanded.

In this case, one side surface of the third cuff 52 comes into close contact with the second tube 20, and if the third cuff 52 is expanded, it becomes expanded in the opposite direction to the direction toward which the extended port on 21 is bentedly extended.

If the extended portion 21 is inserted into the bronchus of one side lung, that is, the third cuff 52 becomes expanded toward the bronchus of the other side lung, which will be discussed later.

Hereinafter, an explanation on the use example of the double lumen endotracheal tube 1 according to the present invention will be given with reference to the attached drawings.

Figure 4:
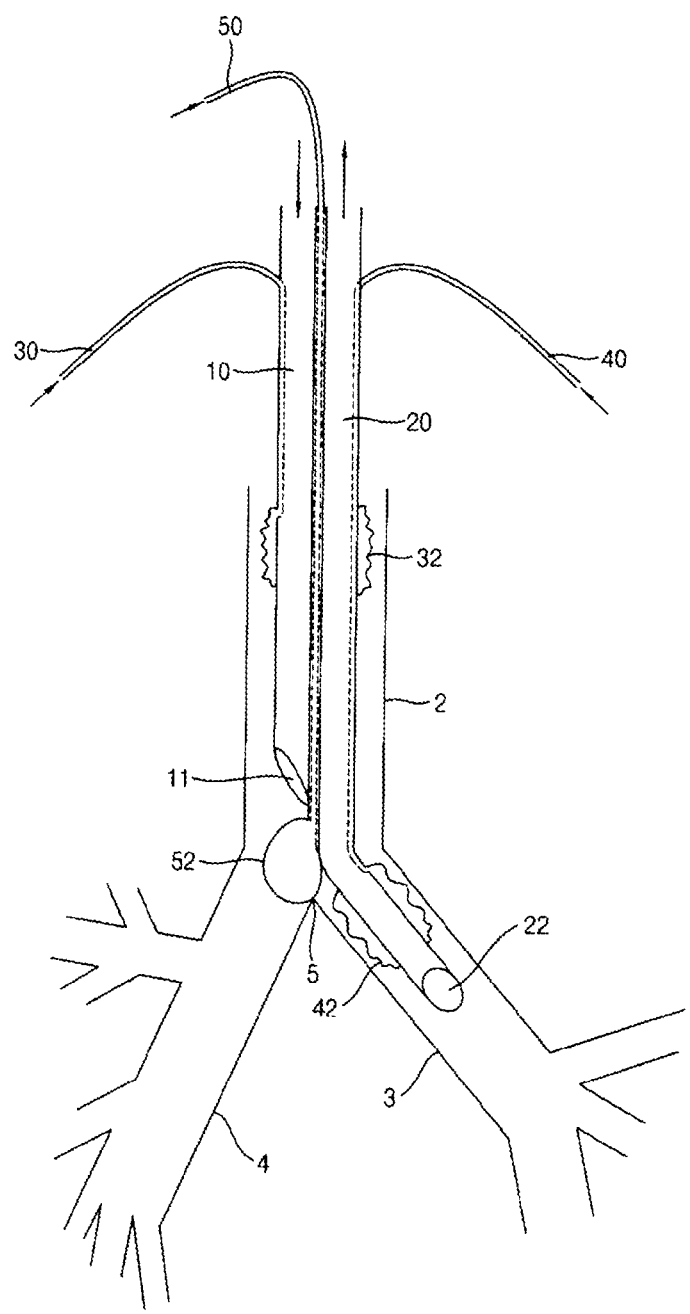
FIG. 4 is an exemplary view showing a state where the double lumen endotracheal tube of FIG. 2 is mounted into the trachea and the left main bronchus.

FIG. 4 is an exemplary view showing a state where the double lumen endotracheal tube of FIG. 2 is mounted into the trachea and the left main bronchus.

Intubation of the double lumen endotracheal tube 1 is performed before a lung resection operation, so as to stop breathing through the lung to be operated and to induce the breathing only through the lung to be not operated.

As shown in FIG. 4, for example, the double lumen endotracheal tube 1 is inserted into the left lung, and through the double lumen endotracheal tube 1, breathing through any one of both side lungs stops, while breathing through the other lung is being induced.

As shown in FIG. 4, on the other hand, the double lumen endotracheal tube 1 is inserted into the left lung, but it may be inserted into the right lung. In this case, the intubation of the double lumen endotracheal tube 1 is carried out in the reverse location to a location as will be discussed below. Further, the right lung has the number of lobes different from the left lung, and if the double lumen endotracheal tube 1 is inserted into the right lung, the extended portion 21 may have an additional structure in consideration of a relatively short distance between the trachea carina and the first lobe.

Referring to FIG. 4, in case where the intubation of the double lumen endotracheal tube 1 according to the present invention is performed, the double lumen endotracheal tube 1 is inserted through the trachea 2.

Upon the intubation of the double lumen endotracheal tube 1, it is important that the extended portion 21 is mounted into the main bronchus of the left lung, and to do this, the intubation is performed in the state where the third cuff 52 has been expanded. In FIG. 4, the reference numeral 4 refers to the main bronchus of the right lung.

If the third cuff 52 of the double lumen endotracheal tube 1 reaches the trachea carina 5, accordingly, the third cuff 52 is expanded in the opposite direction to the direction toward which the extended portion 21 is bent, so that the third cuff 52 and the extended portion 21 are located over the trachea carina 5.

Since the third cuff 52 and the extended portion 21 are located over the trachea carina 5, in detail, they do not enter anymore, and as shown in FIG. 4, accordingly, the double lumen endotracheal tube 1 is mounted into the trachea carina 5 to an accurate depth.

According to the present invention, the third cuff 52 is expanded in the opposite direction to the direction toward which the extended portion 21 is bent, and if it reaches the trachea carina 5, accordingly, a given resistance is applied to a surgeon's hand to allow further insertion of the double lumen endotracheal tube 1 to stop. Also, it can be checked that the double lumen endotracheal tube 1 is inserted to an accurate location, thereby avoiding a separate checking process through an endoscope.

Figure 5:
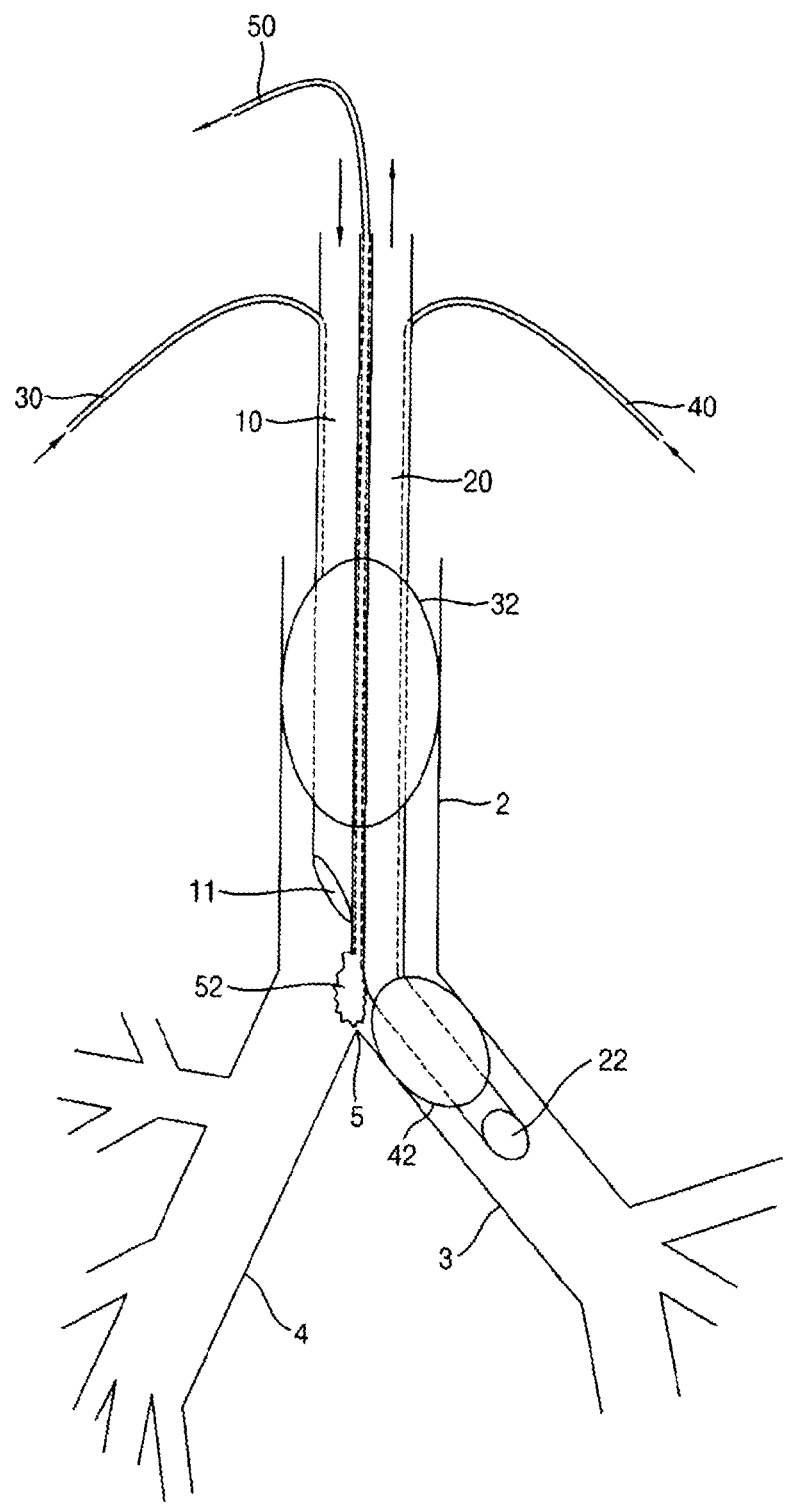
FIG. 5 is an exemplary view showing a state where just after the double lumen endotracheal tube of FIG. 2 is mounted into the trachea and the left main bronchus, a third cuff is contracted and a first cuff and a second cuff are expanded.

FIG. 5 is an exemplary view showing a state where the intubation of the double lumen endotracheal tube of FIG. 2 into the lung is finished.

As shown in FIG. 5, if the third cuff 52 is located over the trachea carina 5, as described above, the accurate mounting of the double lumen endotracheal tube 1 is finished, and the expanded third cuff 52 is contracted by the surgeon.

In this case, the first cuff 32 is expanded in the state of being located in the trachea 2 to close the trachea 2, and the second cuff 42 is expanded in the state of being located in the main bronchus 3 of the left lung to close the main bronchus 3 of the left lung.

Accordingly, breathing of the left lung is performed only through the second tube 20, and breathing of the right lung is performed only through the first tube 10. As a result, breathing through any one side of the left and right lungs stops to conduct the operation for the corresponding lung.

In addition to the first cuff closing the trachea and the second cuff closing one side main bronchus, as described above, the double lumen endotracheal tube according to the present invention includes the third cuff located over the trachea carina, and especially, since the third cuff is over the trachea carina in the state of being expanded, it can easily guide the second end and the second cuff so that they are accurately located in the main bronchus.

On the other hand, the third cuff is expanded toward the opposite side lung to the lung into which the extended portion of the second tube is inserted, and if the third cuff is located over the trachea carina, it can be recognized that the extended portion is accurately inserted into the main bronchus, thereby avoiding a separate checking process through an endoscope to achieve the intubation into the trachea rapidly and easily.

Further, the third cuff is contracted just after it is checked that it is located over the trachea carina, thereby removing space occupation effects caused by the third cuff to start instant breathing through the lung. Moreover, the cuff as a soft structure is utilized to minimize the damage of the bronchus.

Furthermore, the third cuff is expanded with the air received from the third balloon, and in this case, the third balloon penetrates the partition wall between the first tube and the second tube and is connected to the third cuff, so that the structure of the conventional double lumen endotracheal tube can be still utilized, without any attachment of a separate connection tube, thereby achieving excellent universality and usability.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A double lumen endotracheal tube, comprising:
   a first tube extending in one direction;
   a second tube having a straight portion that is secured to the first tube by a partition wall that is located between the first and second tubes and extends along an axial direction, the second tube having an extended portion that is connected to the straight portion and bent toward a preset direction that is different from the axial direction, the second tube being longer than the first tube;
   a first balloon passing through the first tube and configured to expand or contract a first cuff connected to an end of the first balloon;
   a second balloon passing through the second tube and configured to expand or contract a second cuff connected to an end of the second balloon; and
   a third balloon passing through the partition wall and configured to expand or contract a third cuff connected to an end of the third balloon,
   wherein the third cuff is attached to the straight portion of the second tube and located only on a side opposite of the extended portion of the second tube with respect to the axial direction so that the third cuff is capable of expanding toward only a first lung while allowing the extended portion of the second tube to be inserted in a second lung, and
   wherein the third cuff is capable of expanding and being inserted into a trachea so as to reach a tracheal carina and guide an insertion depth of the extended portion of the second tube into the second lung.

2. The double lumen endotracheal tube according to claim 1, wherein the first cuff is adapted to surround outer peripheral portions of the first tube and the second tube and is capable of expanding inside a trachea of a patient to close the trachea of the patient.

3. The double lumen endotracheal tube according to claim 1, wherein the second cuff is adapted to surround an outer peripheral portion of the extended portion of the second tube and is capable of being inserted into a main bronchus of a lung to seal the main bronchus.

\* \* \* \* \*